United States Patent [19]

Loev et al.

[11] Patent Number: 4,490,373

[45] Date of Patent: Dec. 25, 1984

[54] METHOD OF TREATING ASTHMA

[75] Inventors: Bernard Loev, Scarsdale, N.Y.; Richard E. Brown, East Hanover; Fu-chih Huang, Boonton, both of N.J.; Howard Jones, Ossining, N.Y.

[73] Assignee: USV Pharmaceutical Corporation, Tarrytown, N.Y.

[21] Appl. No.: 496,755

[22] Filed: May 20, 1983

[51] Int. Cl.³ .............................................. A61K 31/495
[52] U.S. Cl. .................................... 424/250; 424/251; 424/248.53; 424/267; 424/272; 544/137; 544/368; 544/369; 546/198; 548/217; 548/518; 548/525
[58] Field of Search ............... 424/272, 250, 248.53, 424/251, 272, 267; 544/137, 368, 369; 546/198; 548/217, 518, 525

[56] References Cited

U.S. PATENT DOCUMENTS

| | | | |
|---|---|---|---|
| 3,641,029 | 2/1972 | Wright et al. | 260/268 BC |
| 3,962,441 | 6/1976 | Evans et al. | 424/272 |
| 4,021,440 | 5/1977 | Evans et al. | 424/272 |
| 4,025,637 | 3/1977 | Dunwell et al. | 424/272 |
| 4,269,846 | 5/1981 | Huang et al. | 424/272 |
| 4,298,742 | 11/1981 | Brown et al. | 424/272 |
| 4,405,633 | 9/1983 | Brown et al. | 424/272 |

OTHER PUBLICATIONS

Habib et al., CA 55, 1634f (1961).
Sycheva et al., CA 64, 6633a (1966).
Skraup et al., CA 16, 3660 (1922).
Dickore et al., CA 60, 10694a (1964).
Beilstein, Bd. 27, 2d Revision, pp. 379-381.
Sycheva et al., CA 66, 104936p (1967).
Hack et al., CA 66, 1799f (1967).
Hirono et al., CA 81, 73416x (1974).
Moeller et al., CA 80, 19395f (1974).
Dickore et al., Liebigs Ann. Chem., vol. 733, pp. 70-87 (1970).

Primary Examiner—Leonard Schenkman
Assistant Examiner—Joseph A. Lipovsky

[57] ABSTRACT

A new method of treating asthma is provided. The method is the administration of an effective dose of a Benzoxazole-2-carboxylic acid amide.

14 Claims, No Drawings

METHOD OF TREATING ASTHMA

BACKGROUND OF THE INVENTION (a) Field of the Invention

This invention relates to a new method of treating asthma and, more particularly, to the use of certain heterocyclic amides of use in the treatment of asthma.

(b) Prior Art

Benzoxazole-2-carboxylic acid amides have been described in the literature.

For example, some amides are disclosed in:
1. Habib and Rees, J. Chem. Soc. 3371–3383 (1960) CA 55, 1634i (1961).
2. T. P. Sycheva and M. N. Shchukina, Biol. Aktivn. Soedin., Akad, Navk SSR, 1965, 46–51 CA 64, 6633a (1966)
3. Skraup and Moser, Ber. 55B, 1980–101 (1922) CA 16, 3660 (1922)
4. Farben Fabriken Bayer A.-G. (by Karlfried Dickore, Klaus Sasse, Richard Wegler, and Ludwig Eve). CA 60, 10694a (1964).
5. Beilstein Bd. 27, 2nd Revision, p. 379
6. Wright, William Blythe Jr., Brabander, Herbert J. (American Cyanamid Co.) U.S. Pat. No. 3,641,029, Feb. 8, 1972 CA 76 140882h
7. T. P. Sycheva et al., Khim. Geterotsikl. Soedin. 1966 (4) 506–10 CA 66 104936p (1967)
8. Farben Fabriken Bayer A.-G. (by Helmuth Hack et al.) Belgian No. 659,974, June 16, 1965 CA 66 1977f (1967)
9. Hirono et al. (Nippon Soda Co., Ltd.) Gen. Offen. No. 2,350,907 May 2, 1974 CA 81 73416x (1974)
10. Moeller, Hirnich; Gloxhuber Christian (Henkel and Cie. Gm.b.H) Ger. Offen. No. 2,201,968, Aug. 2, 1973 CA 80 19395f (1974)
11. Karlfriend Dickore et al., Liebigs Ann. Chem 733, 70–87 (1970)

It has now been discovered that certain of the above prior art amides and other new amides are useful in the treatment of asthma.

SUMMARY OF THE INVENTION

This invention relates to a method of treating asthma comprising administering an effective dose of a benzoxazole-2-carboxylic acid amide of the formula

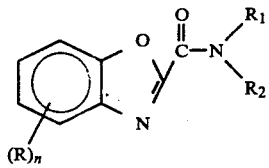

wherein, n is 0–3, each R is independently H, halogen, lower alkyl, trihaloalkyl, lower cycloalkyl, hydroxy, lower alkoxy, cyano, carboxyl or carboxy lower alkyl esters, amino, alkylamino, or dialkylamino; and $R_1$ and $R_2$ are independently H, alkyl, aralkyl, haloaralkyl, alkoxyalkyl, alkylcarboxy or where $R_1$ and $R_2$ together form a ring group with the nitrogen such as piperidino, pyrrolidino, or morpholino, etc. and may contain a hetero atom such as oxygen or sulfur. Preferably, the alkyl or the alkyl, alkoxy, aralkyl or haloaralkyl contains one to twelve carbons and it can be branched or straight-chained. Preferably, the lower cycloalkyl contains three to seven carbon atoms.

It is preferred that n=0–3,

R is H or chlorine, $R_1$ is H, methyl, benzyl or halo-substituted benzyl, $R_2$ is H, $C_1$–$C_6$ alkyl, or alkoxyalkyl of the formula $R_6OC_2H_5$, or an alkyl carboxylic acid or ester of the formula $$CH_2\overset{\overset{O}{\|}}{C}-OR_6$$

wherein $R_6$ is a $C_1$–$C_4$ alkyl or that $R_1$ and $R_2$ with the nitrogen form a ring group.

DETAILED DESCRIPTION OF THE INVENTION

The present heterocyclic amides can be used in the treatment as such or in the form of salts with a wide variety of acids, inorganic and organic, including therapeutically-acceptable acids. The salts with therapeutically-acceptable acids are, of course, useful in the preparation of formulations where water solubility is desired. The salts with therapeutically-unacceptable acids are particularly useful in the isolation and purification of the present amides. Therefore, all acid salts of the present amides are contemplated for use in the present invention.

The pharmaceutically-acceptable acid addition salts are of particular value in therapy. These include salts of mineral acids such as hydrochloric, hydriodic, hydrobromic, phosphoric, metaphosphoric, nitric and sulfuric acids, as well as salts of organic acids such as tartaric, acetric, citric, malic, benzoic, glycollic, gluconic, gulonic, succinic, aryl-sulfonic, e.g., p-toluenesulfonic acids, and the like. The pharmaceutically-unacceptable acid addition salts, while not useful for therapy, are valuable for isolation and purification of the substances. Further, they are useful for the preparation of pharmaceutically-acceptable salts. Of this group, the more common salts include those formed with hydrofluoric and perchloric acids. Mineral acid salts are particularly useful for the preparation of the pharmaceutically-acceptable salts, e.g., the hydrochlorides, by solution in hydrochloric acid and crystallization of the hydrochloride salt formed. The perchloric acid salts are useful for purification and crystallization of the products.

The compounds form conjugates with amino acids and the sugar acids. For example, conjugates can be formed with glucuronic acid, e.g., β-D-glucuronic acid, as well as amino acids especially useful in formulation of therapeutic dosage forms.

As therapeutic agents, the present heterocyclic amides act via inhibition of mediator release. These amides are active orally in the passive cutaneous anaphylaxis (PCA) screen; and inhibit histamine release from passively sensitized rat mast cells (RMC).

According the method of this invention, an effective dose of a Benzoxazole-2-carboxylic acid amide of the above formula is administered to a subject suffering from asthma and in need of treatment.

The therapeutic agents used in this invention may be administered alone or in combination with pharmaceutically-acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered orally in the form of solutions which may contain coloring and flavoring agents or they may be injected parenterally, that is, intramuscularly, intravenously or subcutaneously. For parenteral adminstration, they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-allergy agents and the dosage level is of the same order of magnitude as is generally employed with these other therapeutic agents. The therapeutic dosage will generally be from 10 to 750 milligrams per day and higher although it may be administered in several different dosage units. Tablets containing from 10 to 250 mg. of active agent are particularly useful.

The following example further illustrates the invention.

EXAMPLE 1

N-(Ethoxyethyl)-5-chlorobenzoxazole-2-carboxamide

A mixture of 2-ethoxyethyl 5-chlorobenzoxazol-2-carboxylate (10 g) and 3.5 g of ethoxyethylamine in 10 ml of THF was stirred at room temperature for 2 hours. The precipitated product was filtered and washed well with hexane to give 9 g of product; mp 110°–111° C.

EXAMPLE 2

N-(t-Butoxycarbonylmethyl)-5-chloro-benzoxazole-2-carboxamide

A mixture of 13.5 g of 2-ethoxyethyl 5-chlorobenzoxazol-2-carboxylate and 6.6 g of t-butyl glycine ester in 50 ml of THF was heated at 70° for 2 days. After cooling, the precipitated product was filtered and washed with hexane to give 3 g of product; mp 152°–154° C.

EXAMPLE 3

N-(Carboxymethyl)-5-chlorobenzoxazole-2-carboxamide

Compound from Example 2 (3 g) in 10 ml of trifluoroacetic acid was kept at room temperature overnight. The solvent was removed and ether was added to give 2.9 g of product; mp 222°–224° (dec.).

According to Example 1, the following compounds are similarly prepared.

EXAMPLE 4

N-(Ethoxycarbonylmethyl)-5-chlorobenzoxazole-2-carboxamide; mp 121°–122° C.

EXAMPLE 5

5-Chloro-benzoxazole-2-carboxylic acid N-$\beta$-hydroxyethylpeperazine amide; mp 111°–112° C.

BIOLOGICAL TESTS

The compounds in the following table were shown to be useful in the treatment of asthma when screened according to the Rat Passive Cutaneous Anaphylaxis Screen described in I. Mota, Life Sciences, 7 465 (1963) and Z. Ovary, et al., Proceeding Society of Experimental Biology and Medicine, 81, 548 (1952).

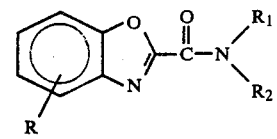

| | | | PCA % I, mg/kg | | | | |
| | | | i.p. | | P.O. | | |
| R | $R_1$ | $R_2$ | 10 | 50 | 1 | 10 | 100 |
| H | H | $C_6H_5$ | | 19 | | | |
| H | H | $CH_3$ | | 68 | | | |
| H | H | $tC_4H_9$ | | 20 | | | |
| H | H | H | | 43 | | | |
| H | $CH_3$ | $CH_3$ | | 82 | | | |
| Cl | 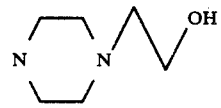 | | | | 24 | 36 | 56 |
| Cl | H | $(CH_2)_2OEt$ | | | 15 | 42 | 52 |
| Cl | H | $CH_2COOC_2H_5$ | 30 | | | | |
| Cl | H | $CH_2COOtC_4H_9$ | 29 | | | | |
| Cl | H | $CH_2COOH$ | 25 | | | | |

We claim:

1. A method of prophylactically treating asthma by administration to an animal in need thereof an effective dose of a compound of the formula

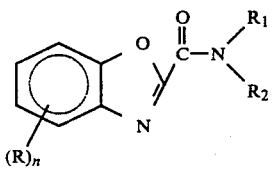

or a pharmaceutically-acceptable acid salt thereof, wherein, n can be 0–3, each R is independently H, halo, lower alkyl, trihaloalkyl, cycloalkyl, hydroxy, lower alkoxy, cyano, carboxyl, a carboxy lower alkyl ester, amino, alkylamino, or dialkylamino, and $R_1$ and $R_2$ are independently H, alkyl, aralkyl, aryl, haloaralkyl, alkoxyalkyl, aminoalkyl, an alkylcarboxylic acid, an alkylcarboxylic acid alkyl ester, or $R_1$ and $R_2$ together can form a piperidino, pyrrolidino, morpholino, piperazino, or beta-hydroxyethyl piperazino ring group with the nitrogen to which $R_1$ and $R_2$ are attached.

2. The method of claim 1 wherein the compound has the formula

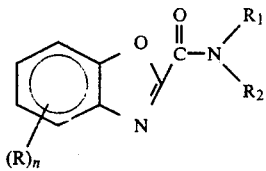

wherein,
n can be 0–3,
each R is independently H, halo, lower alkyl, trihaloalkyl, cycloalkyl, hydroxy, lower alkoxy, cyano, carboxyl, a carboxy lower alkyl ester, amino, alkylamino, or dialkylamino, and
$R_1$ and $R_2$ are independently H, alkyl, alkoxyalkyl, aminoalkyl, an alkylcarboxylic acid or alkylcarboxylic acid alkyl ester, or $R_1$ and $R_2$ together can form a piperidino, pyrrolidino, morpholino, piperazino, or N-beta-hydroxyethylpiperazino ring group with the nitrogen to which $R_1$ and $R_2$ are attached.

3. The method of claim 2 wherein
$R_1$ and $R_2$ are independently H, alkyl, alkoxyalkyl, an alkylcarboxylic acid or an alkylcarboxylic acid alkyl ester, and the alkyl of the alkyl or alkoxy contain one to twelve carbons and the R cycloalkyl contains three to seven carbon atoms.

4. The method of claim 2 which comprises administering a pharmaceutically-acceptable acid salt of a compound of said formula.

5. The method of claim 2 wherein R is H or chlorine.

6. The method of claim 2 wherein $R_1$ is H or methyl.

7. The method of claim 2 wherein $R_2$ is H, an alkyl having 1 to 6 carbons, an alkoxy alkyl of the formula $R_6OC_2H_5$, or an alkyl carboxylic acid or ester of the formula

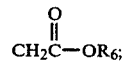

wherein $R_6$ is an alkyl group of 1 to 4 carbon atoms.

8. The method of claim 2 wherein
R is H or chlorine,
$R_1$ is H or methyl, and
$R_2$ is H, alkyl having 1 to 6 carbon atoms, or alkoxyalkyl of the formula $R_6OC_2H_5$, or an alkyl carboxylic acid or ester of the formula

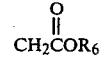

wherein $R_6$ is an alkyl group of 1 to 3 carbon atoms.

9. The method of claim 2 wherein R is H or chlorine, and $R_1$ and $R_2$ together form a ring group.

10. The method of claim 1 wherein the compound is 5-chloro-benzoxazole-2-carboxylic acid N-β-hydroxyethylpiperazine amide.

11. The method of claim 1 wherein the compound is N-(Ethoxyethyl)-5-chlorobenzoxazole-2-carboxamide.

12. The method of claim 1 wherein the compound is N-(Ethoxycarbonylmethyl)-5-chlorobenzoxazole-2-carboxamide.

13. The method of claim 1 wherein the compound is N-(t-butoxycarbonylmethyl)-5-chloro-benzoxazole-2-carboxamide.

14. The method of claim 1 wherein the compound is N-(Carboxymethyl)-5-chlorobenzoxazole-2-carboxamide.

* * * * *